United States Patent [19]
Braynin et al.

[11] Patent Number: 5,242,606
[45] Date of Patent: Sep. 7, 1993

[54] SAMPLE METERING PORT FOR ANALYTICAL ROTOR HAVING OVERFLOW CHAMBER

[75] Inventors: Boris Braynin, Mountain View; Tammy L. Burd, Fremont; Steven Buhl, Cupertino; Carol T. Schembri, San Mateo, all of Calif.

[73] Assignee: Abaxis, Incorporated, Mountain View, Calif.

[21] Appl. No.: 783,041

[22] Filed: Oct. 29, 1991

Related U.S. Application Data

[63] Continuation-in-part of Ser. No. 532,524, Jun. 4, 1990, Pat. No. 5,061,381.

[51] Int. Cl.$^5$ .......................................... B01D 17/038
[52] U.S. Cl. ...................... 210/787; 210/380.1; 422/72; 422/119; 436/45; 436/180; 494/17
[58] Field of Search ................. 73/863.45, 864.72; 210/787, 789, 94, 97, 137, 512.1, 513, 800, 804, 806, 86, 248, 745, 380.1; 422/72, 119; 427/2, 156; 436/45, 180; 494/10, 16, 37, 43, 256, 17

[56] References Cited

U.S. PATENT DOCUMENTS

| | | | |
|---|---|---|---|
| 3,864,089 | 2/1975 | Tiffany et al. | 422/72 |
| 3,873,217 | 3/1975 | Anderson et al. | 422/72 |
| 3,899,296 | 8/1975 | Mailen et al. | 422/72 |
| 3,901,658 | 8/1975 | Burtis et al. | 422/72 |
| 4,035,156 | 7/1977 | Shumate, II | 210/380.1 |
| 4,225,558 | 9/1980 | Peterson et al. | 422/64 |
| 4,279,862 | 7/1981 | Bretaudiere et al. | 422/72 |
| 4,284,602 | 8/1981 | Kelton et al. | 422/72 |
| 4,689,203 | 8/1987 | Kaartinin et al. | 422/72 |
| 4,740,472 | 4/1988 | Burtis et al. | 210/787 |
| 4,847,205 | 7/1989 | Burtis et al. | 422/72 |
| 4,868,129 | 9/1989 | Gibbons et al. | 436/180 |
| 4,876,203 | 10/1989 | Guigan | 436/45 |
| 4,963,498 | 10/1990 | Hillman et al. | 422/72 |
| 5,061,381 | 10/1991 | Burd | 210/789 |
| 5,104,813 | 4/1992 | Besemer et al. | 436/180 |
| 5,160,702 | 11/1992 | Kopf-Sill et al. | 422/72 |
| 5,173,193 | 12/1992 | Schembri | 210/745 |
| 5,186,844 | 2/1993 | Burd et al. | 436/180 |

*Primary Examiner*—Joseph W. Drodge
*Attorney, Agent, or Firm*—Townsend and Townsend Khourie and Crew

[57] ABSTRACT

An analytical rotor for separating plasma whole blood comprises a rotor body having a sample application port in an upper surface thereof. Blood introduced to the sample application port is metered into a metering chamber by capillary flow while the rotor remains stationary. Excess blood passes into an overflow chamber by capillary flow, either simultaneously with the metered flow or after opening of a vent in the overflow chamber. Subsequent rotation of the rotor causes metered blood in the metering chamber to flow into a receiving chamber, typically a plasma separation chamber.

21 Claims, 7 Drawing Sheets

SAMPLE METERING PORT FOR ANALYTICAL ROTOR HAVING OVERFLOW CHAMBER

This patent application is a continuation-in-part of application Ser. No. 07/532,524 filed Jun. 4, 1990 now U.S. Pat. No. 5,061,381 issued Oct. 29, 1991, the full disclosure of which is incorporated herein by reference.

BACKGROUND OF THE INVENTION

1. Field of the Invention

The present invention relates generally to apparatus and methods for separating cellular material from biological fluids and, more particularly, to the design and use of a centrifugal rotor which is capable of separating plasma from a measured volume of whole blood and optionally distributing the plasma to a plurality of test wells within the rotor.

Blood tests frequently require that potentially-interfering cellular components of the blood be separated from the blood plasma prior to testing of the plasma. It is also frequently desirable to divide the separated blood plasma into a plurality of discrete aliquots so that a variety of tests or assays may be performed on the blood. Such separation and division steps have heretofore been typically performed by centrifugation to separate the blood plasma from the cellular components, followed by manual or automated pipetting of the blood plasma into separate test wells. Such procedures are labor intensive and time-consuming, and various automated systems and methods have been proposed for providing multiple aliquots of plasma suitable for testing in a more efficient manner.

Of particular interest to the present invention are centrifugal rotors which have been modified both to separate plasma from whole blood and to distribute the separated plasma into separate test wells. The use of such rotors can provide a plurality of discrete plasma volumes which may be tested or evaluated, all present within the centrifugal rotor, greatly enhancing the efficiency of automated testing procedures.

Although a significant improvement over prior manual or partly manual procedures, previous modified centrifugal rotors have suffered from a number of deficiencies. Such rotors have frequently required the application of relatively large volumes of whole blood in order to achieve the desired separation and distribution. Moreover, such rotors have frequently utilized complex designs which are difficult and costly to manufacture. Often, the rotors require various separable parts or components which are brought together or separated at different points in the centrifugation procedure. Previous centrifugal rotors have often required the user to manually measure a volume of sample prior to applying the sample to the rotor. The need to manually measure the sample volume can significantly decrease the efficiency of an otherwise automated process.

For these reasons, it would be desirable to provide improved centrifugal rotors and methods suitable for separating blood into plasma and cellular components and for further distributing the separated plasma into a plurality of discrete test wells within the rotors. The rotors and methods should be capable of metering precise quantities of blood without requiring the user to premeasure the volume being applied to the rotor. The rotor design should be simple and amenable to low-cost manufacturing procedures, and it would be further desirable if the rotors were of unitary construction with no separable or movable parts.

2. Description of the Background Art

U.S. Pat. No. 4,284,602 describes a centrifugal rotor which measures a predetermined amount of fluid by filling a measuring chamber with fluid under centrifugal force to a certain level, wherein an overflow passage allows excess fluid to flow to an outlet. U.S. Pat. No. 4,876,203 describes a centrifugal rotor which measures a predetermined quantity of fluid by filling a calibrated cell through a capillary duct from a storage chamber, the excess fluid flowing from the calibrated cell through a second capillary duct to an overflow chamber. U.S Pat. No. 3,901,658 describes a centrifugal rotor which measures predetermined volumes of blood by filling a plurality of measuring chambers with blood under centrifugal force, the excess blood flowing into an overflow passageway when a certain centripetal level is reached. U.S. Pat. No. 3,899,296 describes a centrifugal rotor which measures a discrete volume of blood by filling a passageway with blood under centrifugal force, wherein excess blood flows into an overflow chamber, and a ball check is used to seal off the inlet of the passageway after it has been filled. Other centrifugal rotors are described in U.S. Pat. Nos. 3,864,089, 3,873,217, 4,035,156, 4,225,558, 4,279,862 and 4,689,203.

SUMMARY OF THE INVENTION

According to the present invention, an improved analytical rotor capable of metering a discrete quantity of fluid comprises a rotor body having a sample application port into which a fluid sample, e.g. whole blood, can be introduced without prior measurement by the human operator. Connected to the sample application port are a metering chamber and an overflow chamber, each configured to permit a capillary flow of fluid from the sample application port. By configuring the chambers to provide a higher flow rate of fluid from the sample application port into the metering chamber than from the sample application port into the overflow chamber, the metering chamber will preferentially be filled. Alternatively, flow into the overflow chamber can be initially blocked, e.g., by preventing venting of the overflow chamber, to permit complete filling of the metering chamber prior to flow of excess fluid into the overflow chamber.

In a first exemplary embodiment, the portion of the metering chamber which connects to the sample application port is of larger cross-sectional flow area than the cross-sectional flow area of the region connecting the overflow chamber to the sample application port, causing fluid to flow more rapidly into the metering chamber than into the overflow chamber Thus, the metering chamber will fill entirely with fluid and excess will continue to flow into the overflow chamber. In a second exemplary embodiment, a vent is provided in each of the overflow chamber and the metering chamber. When fluid is introduced into the sample application port, the vent in the metering chamber is open, while the vent in the overflow chamber is closed, causing the fluid to flow only into the metering chamber. Once the metering chamber is filled, the vent in the overflow chamber is opened, causing any remaining fluid in the sample application port to flow into the overflow chamber.

In a specific aspect of the present invention, the metering chamber is provided with an indicator which indicates that the metering chamber is filled with fluid.

The indicator may consist of a transparent window, through which the quantity of fluid in the metering chamber can be detected by the human operator or an instrument.

In a further specific aspect of the present invention, a receiving chamber is situated radially outward from the metering chamber and is connected to the metering chamber by a non-capillary passage. Because the passage has no capillary effect, the metering chamber can completely fill without passing fluid into the receiving chamber. Once the metering chamber is filled, the rotor may be spun to cause the fluid in the metering chamber to flow radially outward into the receiving chamber. In a particular embodiment, the receiving chamber is a separation chamber for separating cellular components of whole blood to produce plasma. In some cases, the rotor may include a plurality of metering chambers and receiving chambers. This allows various or multiple tests to be performed on a single sample.

According to the method of the present invention, an unmeasured volume of fluid is introduced to a sample application port in an analytical rotor. A portion of the fluid flows into and fills a metering chamber by capillary action. Excess fluid flows into an overflow chamber, also by capillary action, while the rotor remains stationary. The rotor may then be spun to transfer the metered volume of fluid in the metering chamber to a receiving chamber.

The invention and objects and features thereof will be more readily apparent from the following detailed description and appended claims when taken with the drawings.

DESCRIPTION OF THE SPECIFIC EMBODIMENTS

Figure 1:
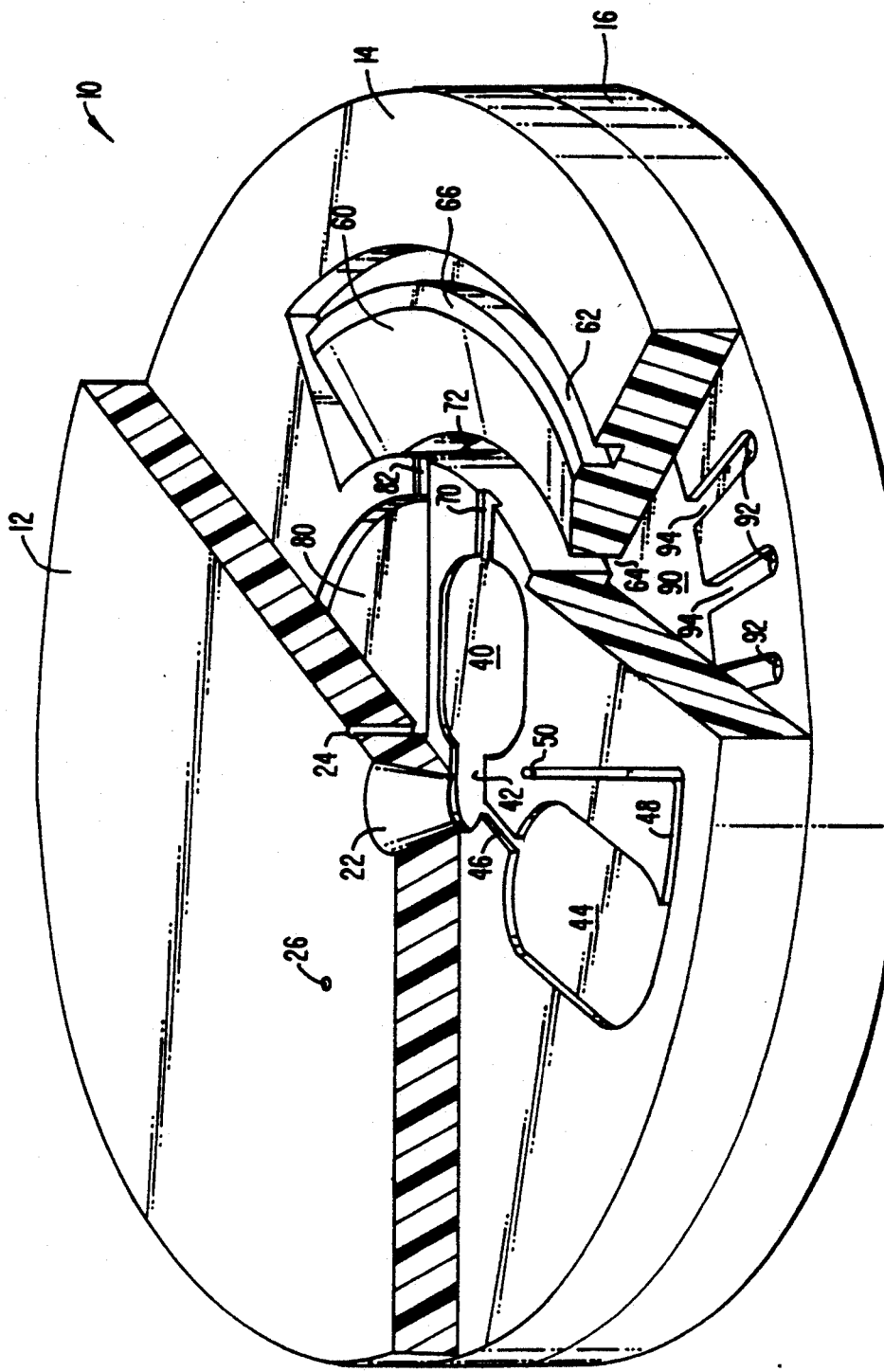
FIG. 1 is a perspective view of a Centrifugal rotor constructed in accordance with the principles of the present invention, with portions broken away.

The present invention provides apparatus and methods for separating cellular components from biological fluids, and in particular for separating whole blood into plasma which may then be subjected to a wide variety of analytic procedures. Conveniently, the apparatus and methods will also provide for distribution of the separated plasma into a plurality of test wells within the rotor so that different analytic procedures may be performed without having to transfer aliquots of the plasma from the apparatus. The apparatus and method are able to separate very low volumes of blood, usually as low as about 0.03 cc, frequently as low as about 0.015 cc, and sometimes as low as about 0.005 cc, although the present invention is suitable for separating much larger volumes as well. The present invention does not require the use of a displacement medium for effecting the desired separation and distribution, and the apparatus design is very simple with no separate or moving parts required. Of course, it may be desirable in certain circumstances to provide such separate or moving parts, but they are not required in order to achieve the blood separation according to the method of the present invention. As a result, the apparatus is very easy to manufacture and can be produced at a very low cost, making the apparatus suitable for use as a disposable in testing whole-blood samples. The apparatus and method are able to separate precise volumes of blood without the need to premeasure the amount applied to the apparatus. The apparatus can further provide for automatic combination of the separated plasma with a reagent or diluent and can apportion substantially equal volumes of plasma among the plurality of test wells. In addition, the apparatus is suitable for use with a variety of conventional analytic measurement devices, such as spectrophotometers and fluorometers, which allow the plasma in the test wells to be individually examined without the need to remove the plasma from the wells.

Although the present invention is particularly suitable for separating cells from blood to produce plasma, it will be useful with a wide variety of other biological fluids, such as urine, sputum, semen, saliva, ocular lens fluid, cerebral fluid, spinal fluid, amniotic fluid, and tissue culture media, as well as food and industrial chemicals, and the like, where it may be desirable to separate cells and other interfering substances prior to analysis or assay.

The apparatus of the present invention includes a centrifugal rotor which is capable of being mounted on a conventional laboratory centrifuge of the type which is commercially available from suppliers, such as Beckman Instruments, Inc., Spinco Division, Fullerton, Calif.; Fisher Scientific, Pittsburgh, Pa.; VWR Scientific, San Francisco, Calif., and the like. Generally, the centrifugal rotors will include a receptacle or other coupling device suitable for mounting on a vertical drive shaft within the centrifuge. The particular design of the receptacle or coupling device will depend on the nature of the centrifuge, and it will be appreciated that the centrifugal rotor of the present invention may be adapted to be used with most types of centrifuges which are now available or which may become available in the future.

The centrifugal rotor comprises a body structure which maintains a desired geometric pattern or relationship between a plurality of chambers and interconnecting passages, as described in more detail hereinbelow. Usually, the body will be a substantially solid plate with the chambers and passages formed as spaces or voids in an otherwise solid matrix. Conveniently, such solid plate structures may be formed by laminating a plurality of separately formed layers together into a composite structure where the chambers and passages are generally formed between adjacent layers. The individual layers may be formed by injection molding, machining, and combinations thereof, and will usually be joined together, typically using a suitable adhesive or by ultrasonic welding. The final enclosed volumes are formed when the layers are brought together. Of course, the centrifugal rotor could also be formed as a plurality of discrete components, such as tubes, vessels, chambers, etc., arranged in a suitable structural framework. Such assemblies, however, are generally more difficult to manufacture and are therefore less desirable than those formed in a substantially solid plate.

The centrifugal rotor may be formed from a wide variety of materials and may optionally include two or more materials. Usually, the materials will be transparent so that the presence and distribution of blood, plasma, and other reagents, may be observed within the various internal chambers and passages. Also, it is generally required that the test wells formed within the rotor have suitable optical paths formed therethrough so that the contents of the test well may be observed spectrophotometrically, fluorometrically, or by other visual assessment instruments. In the exemplary embodiment described below, the rotor is formed from acrylic resins having the required optical properties, at least in those areas which define the optical paths.

The apparatus and method of the present invention are suitable for performing a wide variety of analytic procedures which are beneficially or necessarily performed on blood plasma. The analytic procedures will generally require that the blood plasma be combined with one or more reagents so that some visibly detectable change occurs in the plasma which may be related to measurement of a particular component or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed in the test wells. Generally, however, such assay procedures must be homogeneous and not require a separation step. In other cases, it will be possible to accommodate heterogeneous assay systems by providing a means to separate blood plasma from the test wells after an immunological reaction step has occurred.

Conventional blood assays which may be performed include glucose, lactate dehydrogenase, serum glutamic-oxaloacetic transaminase (SGOT), serum glutamic-pyruvic transaminase (SGPT), blood urea (nitrogen) (BUN), total protein, alkalinity, phosphatase, bilirubin, calcium, chloride, sodium, potassium, magnesium, and the like. This list is not exhaustive and is intended merely as being exemplary of the assays which may be performed using the apparatus and method of the present invention. Usually, these tests will require that the blood plasma be combined with one or more reagents which result in a visually detectable, usually photometrically detectable, change in the plasma. The reagents which are required are well known and amply described in the patent and scientific literature.

Referring now to FIGS. 1-6, a centrifugal rotor 10 constructed in accordance with the principles of the present invention will be described in detail. The rotor 10 is in the form of a substantially solid disk including a top layer 12, middle layer 14, and bottom layer 16 laminated together to form a composite structure. Typically, each of the layers 12, 14, and 16 will be composed of the same material, usually a transparent plastic such as an acrylate, but it is possible that the layers will be composed of different materials and that each layer may include two or more different materials forming different portions of the layer. The exposed surface of top layer 12 will be referred to as the top surface while the exposed surface of the bottom layer 16 will be referred to as the bottom surface. A receptacle 18 is formed in the bottom surface of layer 16 and is generally aligned with the vertical axis 20 of the rotor, as best observed in FIGS. 3 and 4. The receptacle 18 is formed to mate with the drive shaft of a conventional centrifuge system, as described previously.

The top surface 12 includes a blood application port 22 and four vent ports 24, 26, 28, and 30. The blood application port 22 and vent ports 24, 26, 28, and 30, penetrate the entire thickness of the top layer 12 and, as described in more detail hereinbelow, are aligned with various chambers formed in the middle layer 14 of the rotor 10. These penetrations may conveniently be formed in the top layer 12 by machining, e.g., drilling.

The upper surface of middle layer 14 includes a plurality of chambers and passages formed therein. The chambers and passages may be formed by machining a disk having generally flat surfaces or may be formed by injection molding of a suitable plastic resin in order to initially form the disk.

The middle layer 14 includes a metering chamber 40 having an inlet segment 42 which is generally aligned with the blood application port 22 in top layer 12. The metering chamber 40 is connected to an overflow chamber 44 by a connecting passage 46, with the overflow chamber being located radially outward from the metering chamber. A vent connector passage 48 extends from the radially-outward end of overflow chamber 44, first in a generally annular direction and thereafter in a generally radially-inward direction. The distal terminus 50 of passage 46 is aligned with vent port 28 in top layer 12 so that the outward radial extremity of overflow chamber 44 will be vented to the atmosphere during use of the rotor 10.

The depth of metering chamber 40 and overflow chamber 44 will be selected to provide for capillary dimensions when the chambers are completed by lamination of the top layer 12. Typically, the depth will be in the range from about 0.1 to 1.0 mm, more typically being in the range from about 0.25 to 0.75 mm. Usually, the depth will be uniform for both chambers 40 and 44 as well as the connecting passage 46, although it will be possible to vary the depth so long as capillarity is maintained.

A separation chamber 60 is formed in the upper surface of middle layer 14 and is disposed radially outward from the metering chamber 40. The separation chamber 60 includes a cell trap 62 formed at its radially-outward periphery and a receptacle region 65 formed along its radially-inward perimeter. A capillary region 66 is formed between the receptacle region 65 and the cell trap 62 in order to inhibit the backflow of cells after they have entered the cell trap 62 as a result of centrifugal separation. The receptacle region 65 provides a volume which is capable of receiving whole blood or other biological fluid (optionally combined with a diluent or reagent) and which retains the blood plasma or other separated fluid after centrifugation has been completed. An axial port 64 is conveniently formed as an annular passage which penetrates the entire thickness of middle layer 14 so that separated plasma may flow downward from receptacle region 65 of chamber 60 into a collection chamber 90 formed in bottom layer 16, as described in more detail hereinafter. The geometry of the separation chamber 60 may be varied considerably, as discussed in more detail in connection with FIGS. 1A and 1B, below.

The metering chamber 40 is connected to the separation chamber 60 by a short capillary passage 70 which terminates in a vertical wall 72 which forms the inner surface of axial port 64. Such termination of passage 70 will, of course, terminate the capillarity which would otherwise draw fluid through the passage.

The volume of metering chamber 40 will vary depending on the desired application, but will usually be selected to be as low as possible to provide a desired amount of plasma to each of the test wells formed in bottom layer 16, as described in more detail hereinafter. Typically, the volume of metering chamber 40 will be in the range from about 0.005 to 0.05 cc, more typically being in the range from about 0.030 to 0.040 cc.

The volume of overflow chamber 44 will generally be larger than that of the metering chamber 40 in order to accommodate excess blood which may be applied through blood application port 42. Generally, the volume of the overflow chamber 44 will be at least twice that of the metering chamber 40, typically being three or more times larger.

The volume of separation chamber 60 will be selected to accommodate the expected volume of plasma and optionally reagent or diluent which can flow from the metering chamber 40 and reagent chamber 80 (as described below). Typically, the volume of the receptacle region 65 will be in the range from about 0.1 cc to 1.0 cc. more typically being in the range from about 0.25 cc to 0.50 cc. The volume of the cell trap 62 will depend at least in part on the volume of the receptacle region 65. In order to maximize the efficiency of separation, i.e., increase the amount of plasma obtained from a fixed amount of whole blood, it is desirable that the volume of the cell trap 62 be just large enough to accommodate the largest expected volume of cellular material. For whole blood this can be calculated based on the highest expected hematocrit, where the volume of cell trap 62 will then be the expected percentage of the volume of metering chamber 40. Usually, the volume of cell trap 62 will be from about 100% to 200% of the volume of metering chamber 40.

A reagent chamber 80 is also formed in the upper surface of middle layer 14 and connected to the separation chamber 60 through a capillary passage 82. The reagent chamber 80 will be disposed radially inward from the separation chamber 60 so that flow of reagent or diluent from the reagent chamber to the separation chamber 60 may be effected by spinning the rotor 14, as will be described in more detail hereinafter. As illustrated, the capillary passage 80 terminates with an open channel in wall 72. In this way, flow of reagent from chamber 80 will not occur in the absence of outward centrifugal force resulting from spinning of the rotor 10. In many cases, however, it may be desirable to provide a removable seal or barrier in chamber 82, or contain the reagent within a pouch or other package, to preserve the reagent and further assure that the reagent will not leak from chamber 80. Such a barrier, seal or package will be particularly desirable when the reagent is "prepackaged" into the centrifugal rotor 10 at a central preparation facility and later subjected to shipping, storing, and other handling procedures which might otherwise cause the reagent to degrade or leak.

Figure 3:
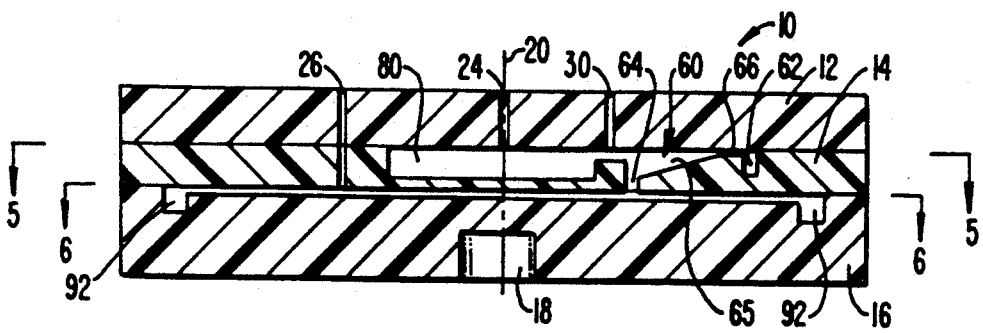
FIG. 3 is a vertical cross-sectional view of the rotor of FIGS. 1 and 2, taken along line 3—3 in FIG. 2.

As best observed in FIG. 3, the reagent chamber 80 may have substantially greater depth than the metering chamber 40 since the ability to provide capillary flow is not necessary. Thus, it is easy to store volumes of reagent which are substantially greater than the volume of blood or plasma which is provided to separation chamber 60 from metering chamber 40.

A collection chamber 90 is formed in the upper surface of bottom layer 16 and is disposed to receive plasma from the axial port 64. A plurality of test wells 92 is formed about the periphery of the collection chamber 90 and connected by short radial passages 94. Generally, the test wells 92 will be spaced equally about the periphery of layer 16 in order to enhance the equal distribution of plasma to each of the test wells. The material above and below each test well 92 will usually be optically transparent in order to provide a clear optical path for visual assessment of the plasma in each well. Alternate optical paths through the rotor 10 may also be provided.

The volume of the test wells 92 will usually be relatively low, typically being in the range from about 0.005 cc to 0.015 cc, more usually being in the range from about 0.008 cc to 0.010 cc. It is possible that liquid, dried, or lyophilized reagents may be provided within the individual test wells so that combination occurs with the plasma when it is introduced. Alternatively, the walls or bottom of the test well 92 may be derivatized with various active components, such as antibodies, antigens, receptors, or the like, which are intended to take part in the analytic procedure.

Figure 1A:
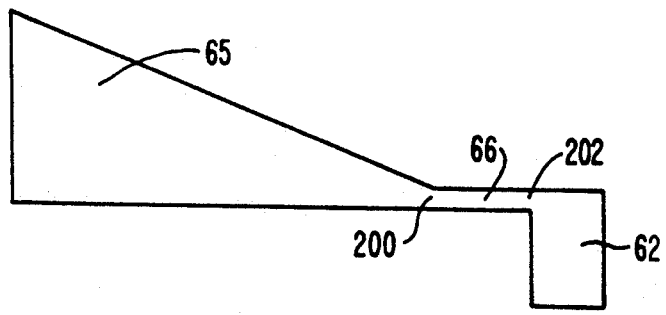
FIGS. 1A and 1B illustrate alternate geometries for a separation chamber of the type employed in a centrifugal rotor constructed in accordance with the principles of the present invention.
Figure 1B:
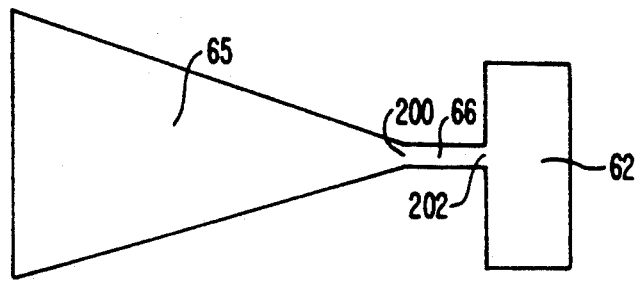
Figure 2:
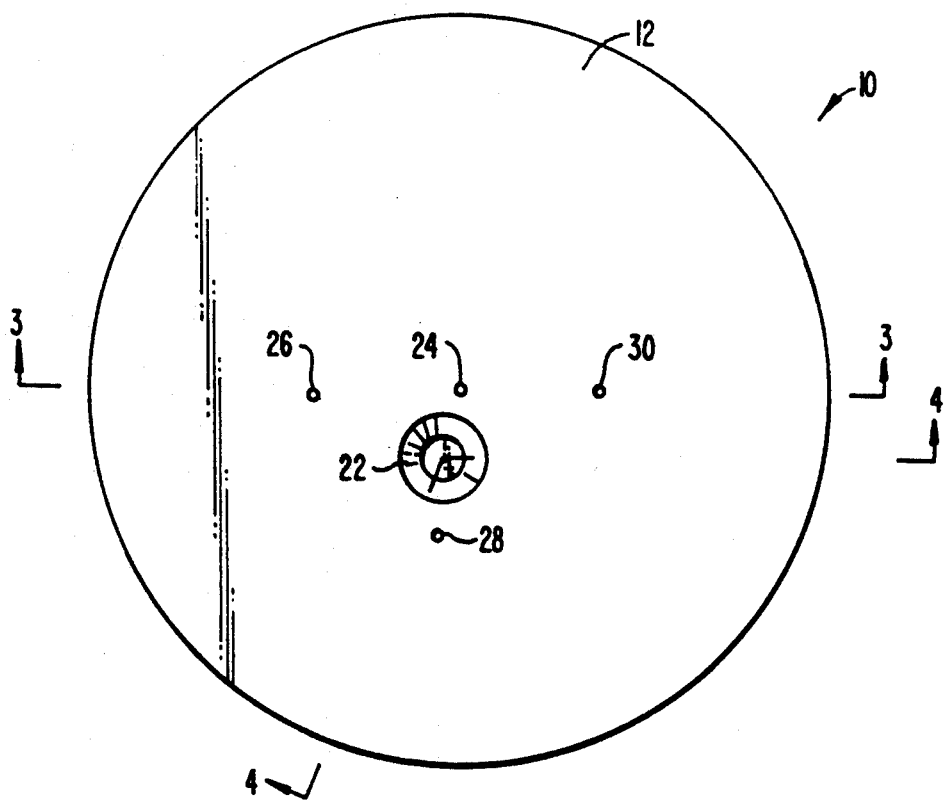
FIG. 2 is a top plan view of the centrifugal rotor of FIG. 1.

Referring now to FIGS. 1A and 1B, the geometry of the separation chamber 60 may be varied considerably within the scope of the present invention. The central feature of the separation chamber 60 is the capillary region 66, which is preferably an annular space having an inner arcuate boundary 200 and an outer arcuate boundary 202. The capillarity of region 66 is broken at each boundary 200 and 202 as the size of the adjoining regions, i.e., receptacle region 65 and cell trap 62, are increased to break the capillarity. Thus, fluid will be unable to flow through the capillary region 66 except when sufficient centrifugal force is applied by centrifugation.

The shapes of the receptacle region 65 and cell trap 62 may vary substantially. The receptacle region 65 will generally be tapered so that the distance between opposed horizontal surfaces increases in the radially inward direction. Such increasing distance provides the desired capillarity break, as discussed above. The taper may be provided by inclining the lower surface relative to the horizontal plane (FIG. 1), inclining the upper surface relative to the horizontal plane (FIG. 1A), or inclining both surfaces (FIG. 1B). The angle between the opposed surfaces of receptacle region 65 is not critical, typically being between 0° and 40°, and usually being between 18° and 22°. The inner arcuate boundary 200 of the capillary region is usually formed contiguously with the narrow end of the tapered receptacle region which defines an arcuate aperture.

The cell trap 62 is typically formed as an annular well which penetrates axially downward in the rotor and which is disposed contiguously with the outer arcuate boundary 202 of the annular space of the capillary region 66. The cell trap 62, however, may also extend upwardly, as illustrated in FIG. 1B, need not have a true annular shape.

Figure 4:
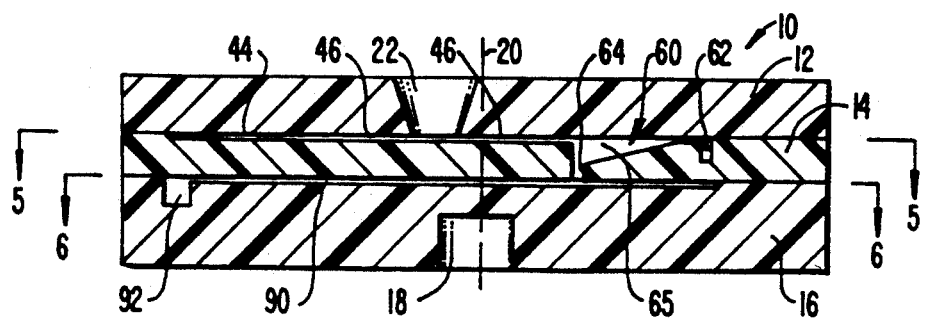
FIG. 4 is a vertical cross-sectional view of the rotor of FIGS. 1 and 2, taken along line 4—4 in FIG. 2.
Figure 4A:
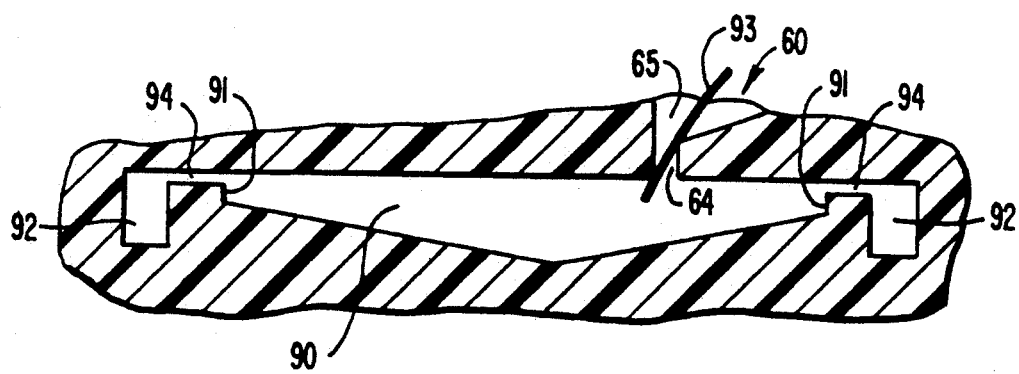
Figure 5:
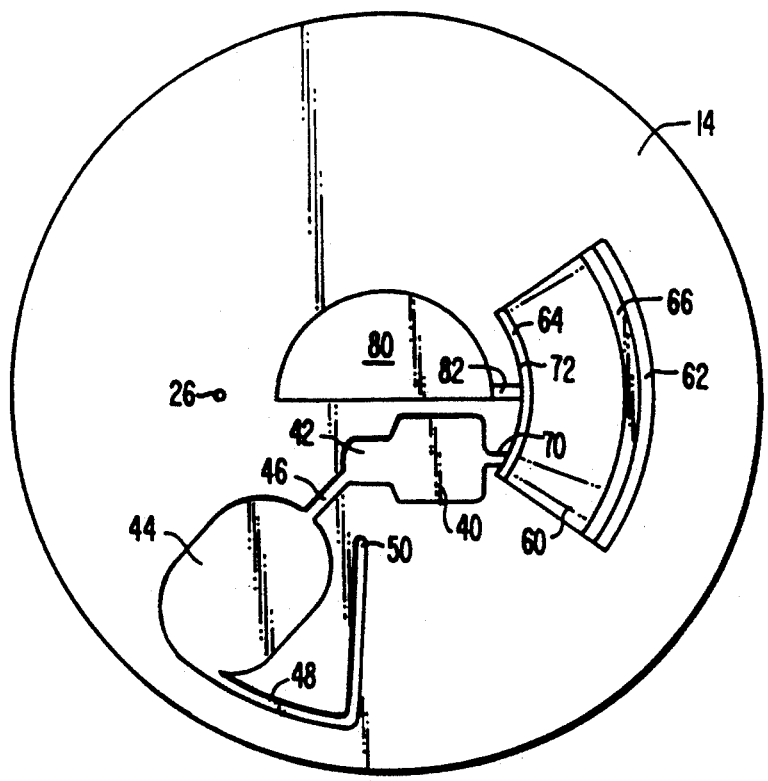
FIG. 5 is a horizontal cross-sectional view of the rotor of FIGS. 1-3, taken along line 5—5 in FIG. 3.
Figure 6:
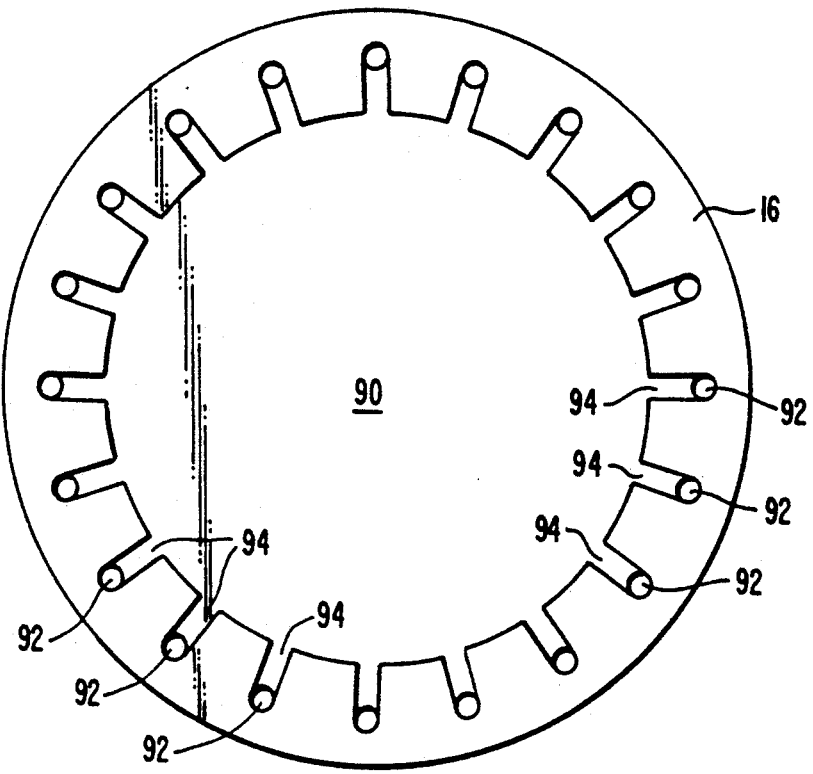
FIG. 6 is a horizontal cross-sectional view of the rotor of FIGS. 1-3, taken along line 6—6 in FIGS. 3 and 4.

Referring now to FIG. 4A, the geometry of collection chamber 90 may be modified to promote mixing of the separated biological fluid, e.g., plasma, with a diluent or reagent combined in separation chamber 60. In particular, the volume of the collection chamber 90 may be increased and a peripheral vertical wall 91 may be provided inside of radial passages 94. Conveniently, the radial passage 94 will be capillaries which serve to prevent loss of fluid from the test wells 92 after the separation and distribution steps are completed. The increased volume of collection chamber 90 and peripheral wall 91 both act to increase the retention time of liquid in chamber 90 as the rotor 0 is spun. Such increased retention time allows more thorough mixing prior to distribution.

In some cases, downward flow of plasma or other separated fluid through axial port 64 may be restricted by surface tension. In such case, it may be desirable to provide means, such as wicking fibers 93, which can disrupt the surface tension and allow the desired flow from receptacle region 65 into the collection chamber 90. Alternatively, the surface tension can be disrupted by abruptly stopping the spinning of the rotor 10 after separation has been achieved. Such cessation of spinning will cause the fluid to wet the wall of the region 65, allowing downflow.

Referring now to FIGS. 7-11, the method of the present invention using the centrifugal rotor 10 as just described will be described in detail. Initially, reagent chamber 80 will be filled with reagent to a desired volume. As illustrated, the chamber 80 is entirely filled, but it is also possible that the chamber will be partially filled. The reagent may be loaded into rotor 10 either at a central preparation facility or immediately prior to use by the user. In the later case, the reagent may be filled using a pipette through vent port 24.

Figure 7:
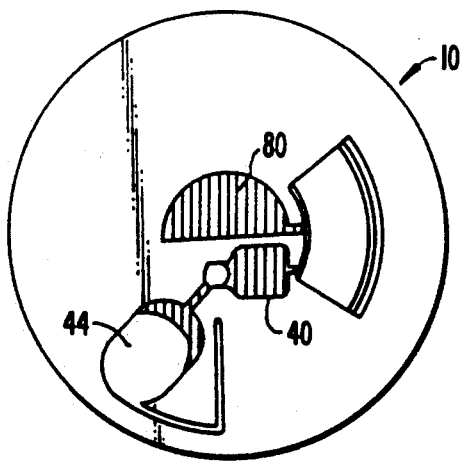
FIGS. 7-11 illustrate the method of the present invention utilizing the centrifugal rotor of FIG. 1.

Whole blood may be loaded onto the rotor 10 through application port 24 in a volume greater than that which can be accommodated by measuring chamber 40. As soon as the blood is applied through port 22, it will begin to flow laterally both into the main portion of chamber 40 and through passage 46 into overflow chamber 44 by capillary action. Since the flow area into measuring chamber 40 is substantially larger than that through passage 46, the measuring chamber will quickly fill with blood, with the overflow passing into overflow chamber 44. In this way, the blood applied through port 22 need not be carefully measured prior to application. After a time sufficient for the blood to partition between measuring chamber 40 and overflow chamber 44, the distribution of blood will be as illustrated in FIG. 7 with the capillary portion of chamber 40 being completely filled and overflow chamber 44 being partially filled.

Figure 8:
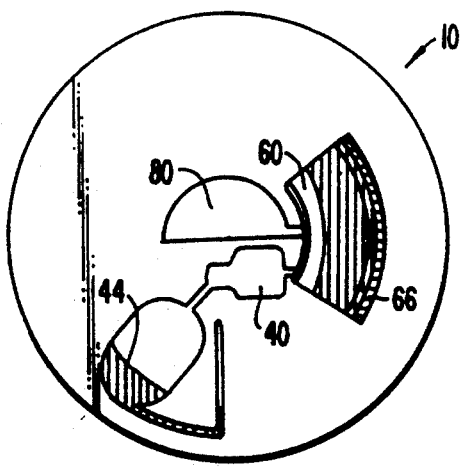

Referring now to FIG. 8, after the reagent has been added to chamber 80 and the whole blood has partitioned between chamber 40 and 44, the rotor 10 will be centrifuged or spun at a rate sufficient to cause the blood from chamber 40 and reagent from chamber 80 to flow into separation chamber 60. Additionally, the blood in overflow chamber 44 will flow radially outward, as illustrated. Conveniently, the rotor 10 will be spun at a rate in the range from about 1500 rpm to 5000 rpm, more usually from about 2500 rpm to 4000 rpm, for a time in the range from about 20 seconds to 5 minutes, more typically being about 1 minute to 3 minutes, so that the cellular components of the blood will flow into trap 66 while the plasma will remain generally in the open portion of separation chamber 60.

Figure 9:
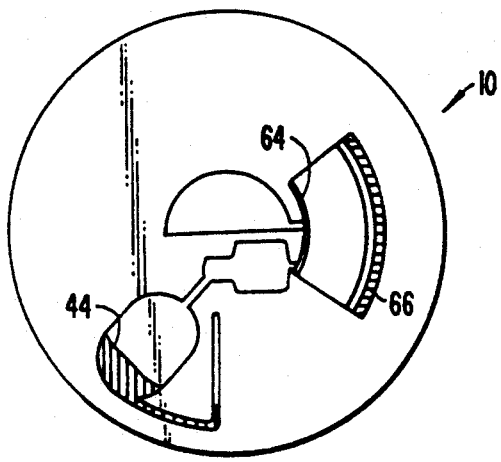
Figure 10:
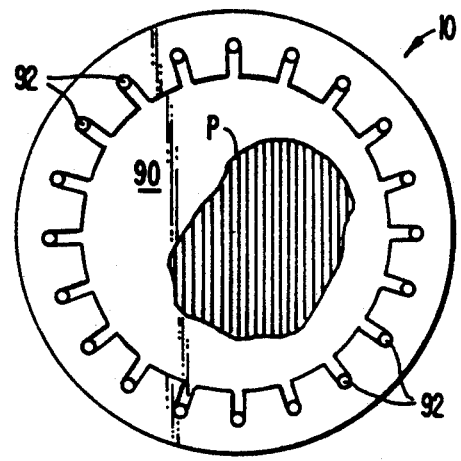
Figure 11:
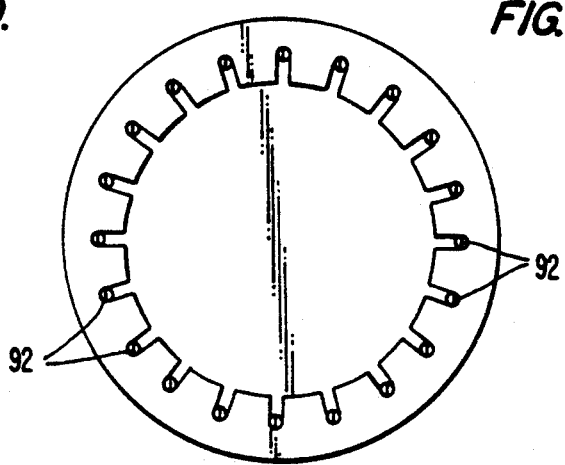

After the separation of plasmas from the cellular components of the whole blood has been completed, spinning of the rotor 10 will be stopped and the separated plasma will flow downward through axial passage 64, as illustrated in FIGS. 9 and 10. The cellular components remain in cell trap 66, and the overflow blood remains in overflow chamber 44 while the plasma has flowed downward into a pool P in collection chamber 90. The plasma may then be distributed substantially equally into the individual test wells 92 by further rotation of the rotor 10, typically at a rate in the range from about 900 rpm to 5000 rpm for a time in the range from about 10 seconds to 1 minute. After the desired distribution has been achieved, the rotor 10 may be removed from the centrifuge and the rotor transferred to an appropriate instrument, such as a spectrophotometer or fluorometer, for testing.

Figure 12:
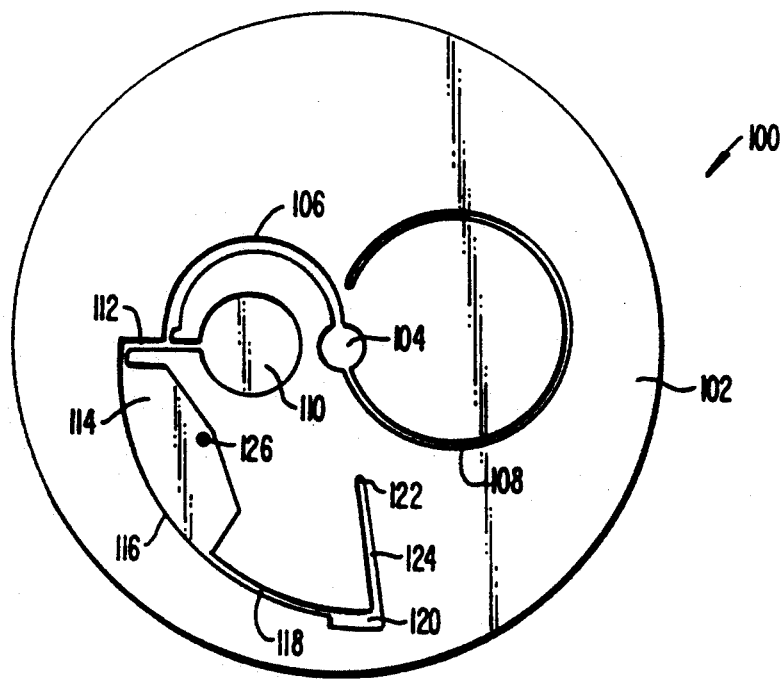
FIG. 12 illustrates an alternate embodiment of the centrifugal rotor of the present invention.

Referring now to FIG. 12, an alternate rotor construction 100 will be described. The rotor 100 will generally be a laminate structure similar to rotor 10, with only a middle layer 102 being illustrated in FIG. 12. The upper layer will include an application port (not illustrated) which is aligned with an entry chamber 104 formed in the upper surface of layer 102. The entry chamber 104 is generally aligned with the vertical (spinning) axis of the rotor 100, and a pair of passages 106 and 108 extend radially outward from said entry port. Chamber 106 serves as the measuring chamber and has a larger cross-sectional area than passage 108 so that it will fill more rapidly. Chamber 108 serves as the overflow chamber so that it can take up any excess blood which is applied through entry chamber 104. A reagent chamber 110 is located radially outward from the entry chamber 104 and connects with a non-capillary passage 112, which is connected with the distal end of chamber 106 and extends generally radially outward.

After blood is applied through entry chamber 104 so that measuring passage 106 is filled and reagent is loaded into chamber 110, the rotor 100 may be spun to cause both the blood from passage 106 and reagent from chamber 110 to flow outward through passage 112 into a separation chamber 114. Continued spinning of the rotor 100 causes the cells generally to collect along the radially-outward wall 116 of chamber 114, and further to flow down a spirally-outward path 118 to collect in cell trap 120. The separation chamber 114 and cell trap 120 are vented through the terminal end 122 of event path 124. Once the desired separation of plasma has been achieved, spinning of the rotor 100 will be stopped, and the plasma allowed to flow downward by gravity through a drainage port 126 formed at the radially-inward periphery of separation chamber 114. Usually, the bottom floor of chamber 114 will be sloped downward in the inward radial direction to promote the drainage of plasma through port 126. A collection chamber will be formed beneath the drainage port 126 in a manner similar to that illustrated in FIGS. 1-6.

Figure 13:
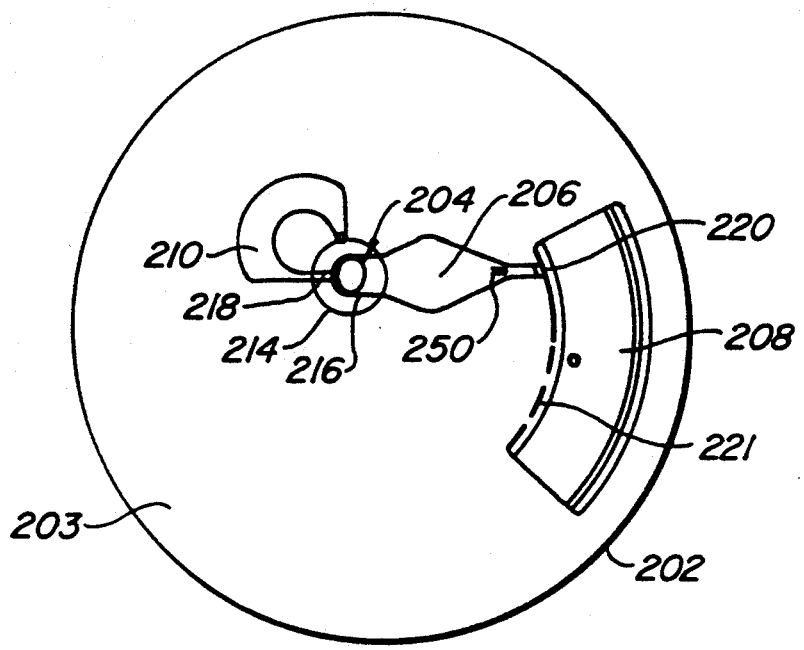
FIG. 13 is a top plan view of an exemplary embodiment of the analytical rotor with metering port, wherein the metering chamber entrance has a larger flow area than that of the overflow chamber entrance.
Figure 14:
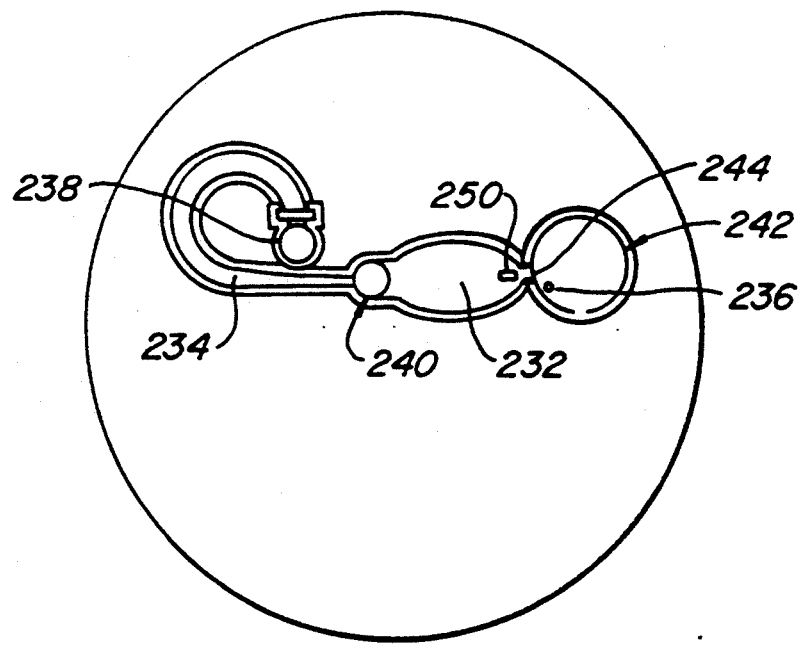
FIG. 14 is a top plan view of an alternative embodiment of the analytical rotor with metering port, showing metering chamber with open vent and overflow chamber with closed vent.

Referring now to FIGS. 13 and 14, an analytical rotor having a fluid metering capability constructed in accordance with the principles of the present invention will be described in detail. A sample application port 204 is situated in an interior portion of an analytical rotor body 202 and opens through a top surface 203 of the analytical rotor body, into which a fluid sample is introduced. A circular ridge 214 extending vertically from the top surface 203 of the analytical rotor 202 and provides a convenient site for placement of a finger in a fingerstick application. In addition, the ridge 214 highlights the location of the entry port to indicate the proper location for introduction of the fluid sample.

A metering chamber 206 is disposed within the rotor body 202 and is positioned radially outward from sample application port 204. The metering chamber 206 has an inlet segment 216 connected to sample application port 204. The cross-sectional dimensions of the inlet segment 216 and the remainder of the metering chamber 206 will be selected to provide capillary flow of the fluid from the application port 204 so that the chamber 206 can be filled while the rotor remains stationary.

An overflow chamber 210 is disposed within the rotor body 202 and is positioned radially outward from sample application port 204 and separated from metering chamber 206. Overflow chamber 210 has a connecting passage 218. The cross-sectional dimensions of the connecting passage 218 and the remainder of the overflow chamber 218 will also be selected to provide capillary flow of fluid from the application port 204 while the rotor remains stationary. Relative flow rates into the metering chamber 206 and the overflow chamber 210 will be controlled, however, so that filling of the metering chamber can be assured with the overflow chamber receiving only excess fluid. In this way, a precisely measured volume of fluid (determined by the volume of the metering chamber) can be provided for subsequent treatment and analysis as described generally above.

Usually, the axial depths of metering chamber 206 and overflow chamber 210 will be selected to provide for capillary dimensions when the chambers are completed by lamination of the top layer of the analytical rotor. Typically, the depth will be in the range from about 0.1 mm to 1.0 mm, more typically being in the range from about 0.25 mm to 0.75 mm. Usually the depth will be uniform for both chambers 206 and 210 as well as inlet segment 216 and connecting passage 218, although it will be possible to vary the depth so long as capillarity is maintained.

A receiving chamber 208 is disposed radially outward from metering chamber 206, and is connected thereto by a passage 220. The passage 220 is constructed so as not to have a capillary effect upon fluid in the metering chamber 206, i.e., the dimensions will be sufficiently large to break the capillarity. This may be accomplished by opening passage 220 into a relatively vertical wall 221 at the junction of passage 220 and the receiving chamber 208, the wall forming an inner wall of receiving chamber 208. In an exemplary embodiment, receiving chamber 208 is a separation chamber for separating cellular components of blood to produce plasma, as described above in connection with prior embodiments.

The volume of metering chamber 206 will vary depending on the desired application, but will usually be selected to be as low as possible to provide a desired amount of fluid to the receiving chamber 208. Typically, the volume of metering chamber 206 will be in the range from about 0.005 cc to 0.05 cc, more typically being in the range from about 0.030 cc 0.040 cc.

The volume of overflow chamber 210 generally will be larger than that of the metering chamber 206 in order to accommodate excess blood which may be applied through sample application port 204. Generally, the volume of the overflow chamber 210 will be at least twice that of the metering chamber 206, typically being 3 or more times larger.

The relative flow rates of fluid into the metering chamber 206 and the overflow chamber 210 may be controlled by adjusting the relative cross-sectional areas of the inlet segment 216 and the connecting passage 218. Conveniently, this can be done by providing an inlet segment 216 which is substantially wider than the connecting passage, as illustrated. In this way, the depths of the metering chamber 206 and the overflow chamber 210 may be maintained within the desired range of capillarity while flow rates can be varied substantially by adjusting the relative widths, with the width of the inlet passage 216 usually being at least twice the width of the connecting passage 218, more usually being at least three times, and frequently being at least four times the width.

Whole blood may be loaded onto the analytical rotor body 202 through sample application port 204 in a volume greater than that which can be accommodated by metering chamber 206. As soon as the blood is applied through sample application port 204, it will begin to flow laterally both into the main portion of metering chamber 206 and into overflow chamber 210 by capillary action (both chambers are vented to permit inflow). Since the flow area into metering chamber 206 is substantially larger than that through overflow chamber 210, the metering chamber will quickly fill with blood, with the overflow passing into overflow chamber 210. Filling of the metering chamber 206 will stop when the fluid reaches the passage 220 which defines a capillary break. Fluid will continue to flow into the overflow chamber 210 until all fluid from the sample application port 204 has been drained. In this way the blood applied through sample application port 204 need not be carefully measured prior to application.

After a time sufficient for the blood or other fluid sample to partition between the measuring chamber 206 and overflow chamber 210, metering chamber 206 will be completely filled and overflow chamber 210 will be partially filled. The analytical rotor 202 is then spun on a centrifuge to cause the blood in metering chamber 206 to move through passage 220 into receiving chamber 208. The blood may then be separated into component parts and subject to analytical tests, as described above in connection with the previous embodiments.

Referring now to FIG. 14, an alternative configuration of a rotor body 230 having a fluid metering capability will be described. In this embodiment, a metering chamber 232 and overflow chamber 234 are each provided with a vent 236 and 238, respectively. The vent 238 in the overflow chamber 234 is constructed so as to be initially closed when the sample is introduced into sample application port 240. By maintaining vent 238 closed, initial flow of fluid from port 240 into the overflow chamber 234 is prevented. Vent 236, however, will be open so that metering chamber 232 can fill prior to any flow into the overflow chamber 234.

The vent 238 will be blocked in a manner that permits its opening (unblocking) by the user at a desired time, as described more fully below. For example, the vent 238 could be covered by a membrane, such as a plastic or metal foil, which can subsequently be pierced or pulled back by the user to open the vent. The vent 236 in the metering chamber 232 will usually be constructed in a permanently open configuration, but could be covered (so long as the user removes the cover before the cover on vent 238 is removed).

Whole blood may be loaded onto the analytical rotor 230 through the sample application port 240 in a volume greater than that which can be accommodated by metering chamber 232. The vent 238 in overflow chamber 210 is kept closed when the blood is applied, while the vent 236 in metering chamber 232 (actually in receiving chamber 242, but connected to metering chamber 232 by connector port 244) remains open, permitting the blood in sample application port 240 to flow only into metering chamber 238. Once metering chamber 232 has been filled, the vent 238 in overflow chamber 234 is opened, permitting any excess blood in sample application port 240 to flow into the overflow chamber. When all of the excess blood has flowed into overflow chamber 234, the rotor 230 may be spun on the centrifuge to cause the fluid in metering chamber 232 to flow through passage 244 into receiving chamber 242 for separation and analysis.

Referring to both FIGS. 13 and 14, an indicator window 250 may be provided in metering chambers 206 and 232, respectively, to permit visual confirmation that the metering chamber has been filled with fluid. The indicator window 250 will typically be a transparent window structure formed in the top surface of the rotor through which the quantity of fluid present in metering chamber 206 is visible. Thus, the operator or an instrument can detect when the metering chamber 206 or 232 is filled with fluid so that the rotor 202 in the first embodiment may be spun to move the fluid to receiving chamber 208, or, in the other embodiment, the vent 238 in overflow chamber 210 may be opened.

When blood which has not been anti-coagulated is to be used, an anticoagulant layer deposited on the interior surfaces of overflow chambers 210 and 234 and metering chambers 206 and 232 helps to prevent clotting of blood before tests have been completed. An anti-coagulant such as lithium heparin is suitable for this purpose.

In order to increase the filling rates of metering chamber 206 or 232 and overflow chamber 210 or 234, a surfactant layer may be deposited on the interior surfaces of the chambers. A surfactant is chosen which does not lyse the blood cells, unless lysis is desired. The surfactant may also be deposited at selected areas along the interior surfaces to create variable filling rates or zones of faster and slower filling rates.

Although the foregoing invention has been described in detail for purposes of clarity of understanding, it will be obvious that certain modifications may be practiced within the scope of the appended claims. In particular, it will be appreciated that two or more metering chambers, separation chambers, or overflow chambers may be provided in order to run simultaneous tests and assays which require different test conditions. For example, multiple metering chambers may be provided to allow combination with different reagents or diluents in isolated separation chambers. Alternatively, a single metering chamber may be connected by separate capillary passages to control flow into separate separation chambers. In either case, assays and tests requiring different protocols can be carried in a single rotor system.

What is claimed is:

1. An analytical rotor comprising:
   a rotor body having generally horizontal top and bottom surfaces, central receptacle means for facilitating rotation of the body about a generally vertical axis, and a sample application port through the top surface;
   a horizontal inlet segment extending from the sample application port in a first direction;
   a horizontal connecting passage extending from the sample application port in a second direction;
   a metering chamber with an interior surface disposed in the rotor body horizontally separated from the sample application port and connected to the sample application port by the inlet segment to receive fluid therefrom;
   an overflow chamber disposed in the rotor body horizontally separated from the sample application port and connected to the sample application port by the connecting passage to receive fluid therefrom; and
   means for selectively directing flow from the sample application port to the metering chamber in preference to the overflow chamber such that the metering chamber will fill entirely with fluid and excess fluid will flow to the overflow chamber while the rotor body remains stationary.

2. An analytical rotor as in claim 1, wherein the metering chamber and the overflow chamber have capillary dimensions to effect capillary flow of fluid for the sample application port.

3. An analytical rotor as in claim 2, wherein the metering chamber has a flow area larger than the flow area of the overflow chamber, such that the fluid flow rate into the metering chamber is higher than the flow rate into the overflow chamber.

4. An analytical rotor as in claim 2, wherein the means for selectively directing flow comprises a first vent in the metering chamber, a second vent in the overflow chamber, and means for selectively blocking the second vent, whereby fluid flows only into the metering chamber until the second vent is unblocked.

5. An analytical rotor as in claim 4, wherein the means for selectively blocking comprises a membrane covering the second vent.

6. An analytical rotor as in claim 1, wherein the means for selectively directing flow comprises a first capillary portion of the inlet segment connecting the measuring chamber to the sample application port and a second capillary portion of the connecting passage connecting the overflow chamber to the sample application port, wherein the first capillary portion has a flow area larger than the flow area of the second capillary portion, such that the fluid flow rate into the metering chamber is higher than the flow rate into the overflow chamber.

7. An analytical rotor comprising:
   a rotor body having generally horizontal top and bottom surfaces, central receptacle means for facilitating rotation of the body about a generally vertical axis, and a sample application port through the top surface;
   a horizontal inlet segment extending from the sample application port in a first direction;
   a horizontal connecting passage extending from the sample application port in a second direction;
   a metering chamber having capillary dimensions and being connected to the sample application port by the inlet segment;
   a receiving chamber disposed radially outward from the metering chamber and being connected to the metering chamber through a passage which does not have capillary dimensions;

an overflow chamber having capillary dimensions and connected to the sample application port by the connecting passage; and means for selectively directing flow from the sample application port to the metering chamber in preference to the overflow chamber, such that the metering chamber will fill entirely with fluid and excess fluid will flow to the overflow chamber while the rotor body remains stationary.

8. An analytical rotor as in claim 7, wherein the metering chamber has a flow area larger than the flow area of the overflow chamber, such that the fluid flow rate into the metering chamber is higher than the flow rate into the overflow chamber.

9. An analytical rotor as in claim 7, wherein the means for selectively directing flow comprises a first vent in the metering chamber, and a second vent in the overflow chamber, and means for selectively blocking the second vent, whereby fluid flows only into the metering chamber until the second vent is unblocked.

10. An analytical rotor as in claim 9, wherein the means for selectively blocking comprises a membrane covering the second vent.

11. An analytical rotor as in claim 7, further comprising means for indicating that the metering chamber has been filled with fluid.

12. An analytical rotor as in claim 11, wherein the means comprises a transparent window through which fluid present in the metering chamber is visible.

13. An analytical rotor as in claim 7, further comprising a layer of anti-coagulant material on the interior surfaces of the chambers selected from the metering chamber and the overflow chamber.

14. An analytical rotor as in claim 7, further comprising a layer of a surfactant on selected interior surfaces of the metering chamber and overflow chamber to increase the filling rates thereof.

15. An analytical rotor as in claim 14, wherein the layer of surfactant is deposited on selected areas of said interior surfaces to create zones of faster and slower filling rates.

16. An analytical rotor as in claim 5, wherein the sample application port has a volume which is larger than the volume of the metering chamber and smaller than the combined volume of the metering chamber and the overflow chamber.

17. An analytical rotor as in claim 7, further comprising at least one additional metering chamber having capillary dimensions and being connected to the sample applicator.

18. An analytical rotor as in claim 7, further comprising a collection chamber disposed beneath the receiving chamber and being connected to the receiving chamber to receive fluid therefrom, the collection chamber comprising a plurality of test wells for separation of the fluid into equal test portions.

19. A method for transferring a metered volume of fluid from a sample application port to a receiving chamber in an analytical rotor, said method comprising:

introducing an unmetered volume of fluid into the sample application port while the rotor remains stationary, whereby the fluid flows by capillary action from the sample application port through an inlet segment in a first generally horizontal direction into a metering chamber having a fixed volume less than the volume of the unmetered volume of fluid until the metering chamber is filled;

flowing by capillary action excess fluid from the sample application port through a connecting passage in a second generally horizontal direction, into an overflow chamber; and rotating the rotor around a central receptacle disposed about a vertical axis to transfer the measured volume of liquid from the metering chamber radially outward to a receiving chamber.

20. The method of claim 19 further comprising the step of opening a vent in the overflow chamber prior to said step of flowing.

21. The method of claim 19 wherein the step of opening includes piercing a membrane which covers the vent.

* * * * *